(12) United States Patent
Georgeson

(10) Patent No.: US 6,848,312 B2
(45) Date of Patent: Feb. 1, 2005

(54) SYSTEM, METHOD AND APPARATUS FOR THE INSPECTION OF JOINTS IN A COMPOSITE STRUCTURE

(75) Inventor: Gary E. Georgeson, Federal Way, WA (US)

(73) Assignee: The Boeing Company, Seattle, WA (US)

( * ) Notice: Subject to any disclaimer, the term of this patent is extended or adjusted under 35 U.S.C. 154(b) by 187 days.

(21) Appl. No.: 10/078,226

(22) Filed: Feb. 18, 2002

(65) Prior Publication Data

US 2003/0154801 A1 Aug. 21, 2003

(51) Int. Cl.$^7$ ................................................ G01N 9/24
(52) U.S. Cl. ........................... 73/627; 73/628; 73/620
(58) Field of Search ..................... 73/596, 597, 598, 73/627, 628, 618, 619, 620, 624, 625, 644, 799

(56) References Cited

U.S. PATENT DOCUMENTS

| | | | | |
|---|---|---|---|---|
| 3,832,889 A | * | 9/1974 | Bauer | 73/642 |
| 4,848,159 A | * | 7/1989 | Kennedy et al. | 73/641 |
| 5,677,490 A | * | 10/1997 | Gunther et al. | 73/622 |
| 5,698,787 A | * | 12/1997 | Parzuchowski et al. | 73/643 |

OTHER PUBLICATIONS

B. Boro Djordjevic, Robert E. Green, Jr.; *Non–Contact Ultrasonic Techniques for Process Control of Composite Fabrication*; NDT.net; Nov. 1997; pp. 1–8; vol. 2, No. 11; Conference on NDE applied to Composite Fabrication; St. Louis, Missouri; available at <http://www.ndt.net/article/aero1197/green/green.htm>.

Mahesh C. Bhardwaj; *High transduction Piezoelectric transducers and introduction of Non–Contact analysis*; NDT.net; Jan. 2000; pp. 1–19; vol. 5, No. 01; available at <http://www.ndt.net/article/v05n01/bhardwaj/bhardwaj.htm>.

B. Boro Djordjevic; *Remote Non–Contact Ultrasonic Testing of Composite Materials*; pp. 1–6; available at <http://www.ndt.net/article/wcndt00/papers/idn358/ind358.htm> (visited Feb. 11, 2002).

QMI, Inc.; *Air–Coupled Ultrasonic Inspection; QMI*; pp. 1–3; available at <http://www.qmi–inc.com/AIRSCAN.htm> (visited Feb. 12, 2002).

QMI, Inc.; *Sonda 007CX—Multifrequency Instrument for Air–Coupled Ultrasonic Testing; QMI*; pp. 1–2; available at <http://www.qmi–inc.com/SONDA.htm> (visited Feb. 12, 2002).

* cited by examiner

Primary Examiner—Edward Lefkowitz
Assistant Examiner—Corey D. Mack
(74) Attorney, Agent, or Firm—Alston & Bird LLP

(57) ABSTRACT

A system for inspecting the joint of a composite structure includes a transmitting transceiver and a receiving transceiver, as well as a processing element. Typically, the composite structure includes first and second panels that are connected to define the joint, with the second panel extending outwardly from the first panel of the joint. Moreover, the composite structure includes a filler disposed at the joint. The transmitting transducer is disposed proximate an input side of the second panel and can transmit an ultrasonic signal into the second panel such that at least a portion of the signal reflects off of the first panel at the joint and exits an output side of the second panel. A receiving transducer disposed proximate the output side of the second panel can receive a reflected portion of the ultrasonic signal. And a processing element is capable of identifying a defect in the composite structure.

23 Claims, 6 Drawing Sheets

US 6,848,312 B2

SYSTEM, METHOD AND APPARATUS FOR THE INSPECTION OF JOINTS IN A COMPOSITE STRUCTURE

FIELD OF THE INVENTION

The present invention relates generally to systems and methods for inspecting joints in a composite structure and, more particularly, to systems and methods for inspecting joints in composite structures utilizing air-coupled transducers.

BACKGROUND OF THE INVENTION

Generally, composite structures are made up of multiple elements. And often, these elements intersect and are interconnected at joints. In this regard, the integrity of these joints is typically critical to the performance of the structure. One very common joint is the T-joint, where one plane of the composite ends at the surface of another. Another, less common joint, is the X-joint, in which two planes intersect one another. For design reasons, the intersections of these elements have some type of external radius (i.e., the intersection does not have sharp corners), and contain an internal filler material, sometimes referred to as a "noodle." The quality of the noodle, its interface with the elements of the composite structure, and the consolidation of the elements, are all critical to proper joint functioning. For example, in the aircraft industry, the quality of the intersection of the webs and flanges in composite spars, or webs and skins in co-cured structures are critical to their performance. Flaws, such as cracks, voids, delaminations, or porosity can form in the joint region and adversely affect the composite structure.

To help ensure the integrity of joints in composite structures, the joints are generally inspected for flaws. Such joints are typically very difficult to inspect, however, particularly using traditional nondestructive inspection (NDI) methods. The techniques that can "see" joint defects require lab-intensive inspections or the use of multiple axis robotic scanners. For example, one NDI method of inspecting radiused joint regions includes using a hand-operated ultrasonic testing (UT) transducer in pulse-echo mode with a radiused shoe mounted on its end. The operator holds the shoe against the inner radius of the joint, sliding it along the length, and rocking it back and forth over a near 90° angle. The operator looks for flaw indications that will affect the ultrasound back to the transducer, which will be picked up and indicated by changes in the amplitude/time trace on an oscilloscope. The operator must determine "on the fly" whether or not the UT reflection amplitude is high enough and, at the same time, whether the extent of the flaw is great enough to disqualify the composite structure. In this regard, the operator generally utilizes a radius flaw standard and a pre-determined NDI criteria for flaw amplitude and length.

While NDI methods including hand-operated UT transducers are adequate for detecting flaws in composite structures, such methods suffer from numerous drawbacks. First, such methods are generally costly and time consuming as the operator is required to operate the hand-operated UT transducer during the entire process. Second, such methods are operator dependent and, as such, are subject to potential operator errors. In this regard, the operator must continuously monitor an oscilloscope for signal changes, while moving the transducer in the radial and axial directions along the joint region. Further, flaw indications are often subtle and, therefore, require tracking at multiple angles with complete coverage often difficult to ensure.

Third, such hand-operated inspection methods do not provide reviewable image data. In this regard, no data is saved for subsequent analysis or review if questions arise subsequent to the inspection. Fourth, such methods do not produce images that show the size or length of any flaw indications that are discovered. The operator simply marks the measured length of an indication on the part itself. Finally, due to the extremely high attenuation of ultrasound by air, a couplant, such as water or a semi-liquid gel, is generally required between the transducers and the composite structure for the UT transducers to work properly. The inclusion of the couplant, however, limits inspections to structures that will not be contaminated by the couplant.

In light of the drawbacks to hand-operated inspection methods, a number of automated (i.e., machine-driven) methods have been developed. One such automated, method, the multiple-transducer automated UT scanning system, makes use of several transducers mounted in a variety of orientations. In this regard, such systems are typically set up for a particular configuration of a particular composite structure. multiple-transducer automated UT scanning systems generally work well for straight, lengthy parts, but they are expensive to manufacture and are relatively inflexible. Such systems also require water squirters to supply couplant between the transducers and the composite structures.

Another automated system makes use of a rotating mirror scanning head mounted to an x-y-z robot to inspect radii. This system eliminates most of the drawbacks of the aforementioned methods, but it too is expensive to implement. Further, such a system is generally difficult to operate, and is sensitive to radius orientation (relative to scanning head) and surface roughness, which affects the ability of the system to couple to the composite structure to receive reliable data.

SUMMARY OF THE INVENTION

In accordance with the present invention, an improved system and methods are provided for inspecting a joint in a composite structure. As such, the system and methods of the present invention can reliably detect defects within the joint. The system and methods of the present invention overcome the drawbacks of other automated inspection systems by inspecting the joint without the use of couplants that could contaminate the composite structure. Further, the system of the present invention is inexpensive to manufacture, when compared to conventional automated systems. And the system and methods of the present invention are inexpensive to implement, as compared to conventional automated inspection systems and methods.

Typically, the composite structure includes first and second panels that are connected to define the joint. The second panel extends outwardly from the first panel of the joint, thereby generally defining a T- or part of an X-shaped composite structure. Moreover, the composite structure includes a filler disposed at the joint. The system and methods of the present invention are therefore designed to reliably detect defects at the joint, such as defects indicative of voids, cracks and/or disbonds within the filler.

The system of the present invention includes a transmitting transducer disposed proximate an input side of the second panel. The transmitting transducer is capable of transmitting an ultrasonic signal into the second panel such that at least a portion of the ultrasonic signal reflects off of the first panel at the joint. The reflected portion of the ultrasonic signal then exits an output side of the second panel. According to the present invention, the input and output sides are on opposite sides of the second panel and are located on a common side of the first panel.

In one embodiment in which the filler is disposed between and at least partially contacts both the first and second panels, the transmitting transducer is capable of transmitting an ultrasonic signal into the filler at an interface of the filler and the second panel. As such, at least a portion of the ultrasonic signal reflects off of the first panel at an interface of the first panel and the filler. For example, the second panel may define a gap at the joint with the filler being disposed within the gap. In this example, the transmitting transducer would transmit the ultrasonic signal into the filler within the gap such that at least a portion of the ultrasonic signal reflects off the first panel at an interface of the filler in the first panel. In one common configuration, the second panel may include a base portion, an upstanding portion and a fillet portion joining the base and upstanding portions. In this configuration, the base portion is disposed parallel to the first panel and the upstanding portion extends outwardly from the first panel. As such, the transmitting transducer will transmit the ultrasonic signal into the filler at the fillet portion of the second panel.

The system also includes a receiving transducer disposed proximate the output side of the second panel. The receiving transducer is capable of receiving a reflected portion of the ultrasonic signal. The system further includes a processing element capable of identifying a defect in the composite structure based upon the relationship of the reflected portion of the ultrasonic signal received by the receiving transducer to a predetermined threshold. In this regard, the processing element is capable of identifying a defect based upon a comparison of the reflected portion of the ultrasonic signal and a predetermined threshold that is based upon the ultrasonic signal transmitted by the transmitting transducer. For example, the processing element may identify a defect when the reflected portion of the ultrasonic signal is less than a predetermined percentage of the ultrasonic signal transmitted by the transmitting transducer.

In one embodiment, the first and second panels each include a plurality of plies that are adhesively bonded together. The second portion generally includes two opposed sheets with each sheet including a plurality of plies. Moreover, each sheet of this embodiment has a base portion, an upstanding portion and a fillet portion joining the base and upstanding portions. The base portions of the sheets are disposed parallel to the first panel and diverge from one another, while the upstanding portions extend outwardly from the first panel. As such, the transmitting transducer is capable of transmitting the ultrasonic signal into the fillet portion of one of the sheets such that at least a portion of the ultrasonic signal reflects off of the first panel at the joint and exits the fillet portion of the other sheet. In this embodiment, the fillet portions of the sheets of the second panel may define a gap at the joint. The filler may be disposed within the gap and the transmitting transducer may be configured to transmit ultrasonic signals into the filler within the gap such that at least a portion of the ultrasonic signals reflect off the first panel at an interface of the filler and the first panel.

The system may also include a scanning assembly electrically connected to the processing element. The transmitting and receiving transducers are secured to the scanning assembly in this embodiment and are guided along the joint by the scanning assembly. The scanning assembly may include a yoke having one end disposed proximate the input side of the second panel and another end disposed proximate the output side of the second panel. In this configuration, the transmitting transducer is secured to the end of the yoke proximate the input side and the receiving transducer is secured to the end of the yoke proximate the output side. In addition to the yoke, the scanning assembly may include a guide assembly capable of moving the yoke relative to the composite structure.

In operation to inspect a joint in a composite structure, ultrasonic signals are transmitted into the input side of the second panel such that at least a portion of the ultrasonic signals reflect off of the first panel at the joint and exit the output side of the second panel. The reflected portion of the ultrasonic signals is then received on the output side of the second panel. A defect may then be identified in the composite structure based upon a relationship between the reflected portion of the ultrasonic signals received and the predetermined threshold. This predetermined threshold is typically based upon the ultrasonic signal that was transmitted and defects may therefore be identified in instances in which the reflected portion of the ultrasonic signals is less than a predetermined percentage of the ultrasonic signals that were transmitted.

Typically, this inspection process involving the transmission of an ultrasonic signal and the reception of the reflected portion of the ultrasonic signal is repeated at a plurality of different points. These points may be spaced longitudinally along the length of the composite structure and/or spaced in a transverse direction, orthogonal to the longitudinal axis defined by an elongate composite structure. As such, the entire joint may be examined in order to reliably detect any defects within the joint. Moreover, the system and methods of the present invention may advantageously inspect joints in composite structures having various configurations, including composite structures having T and X-shapes so long as the composite structure includes a pair of panels connected in a manner to define a joint in which a filler is disposed.

BRIEF DESCRIPTION OF THE DRAWINGS

Figure 1:
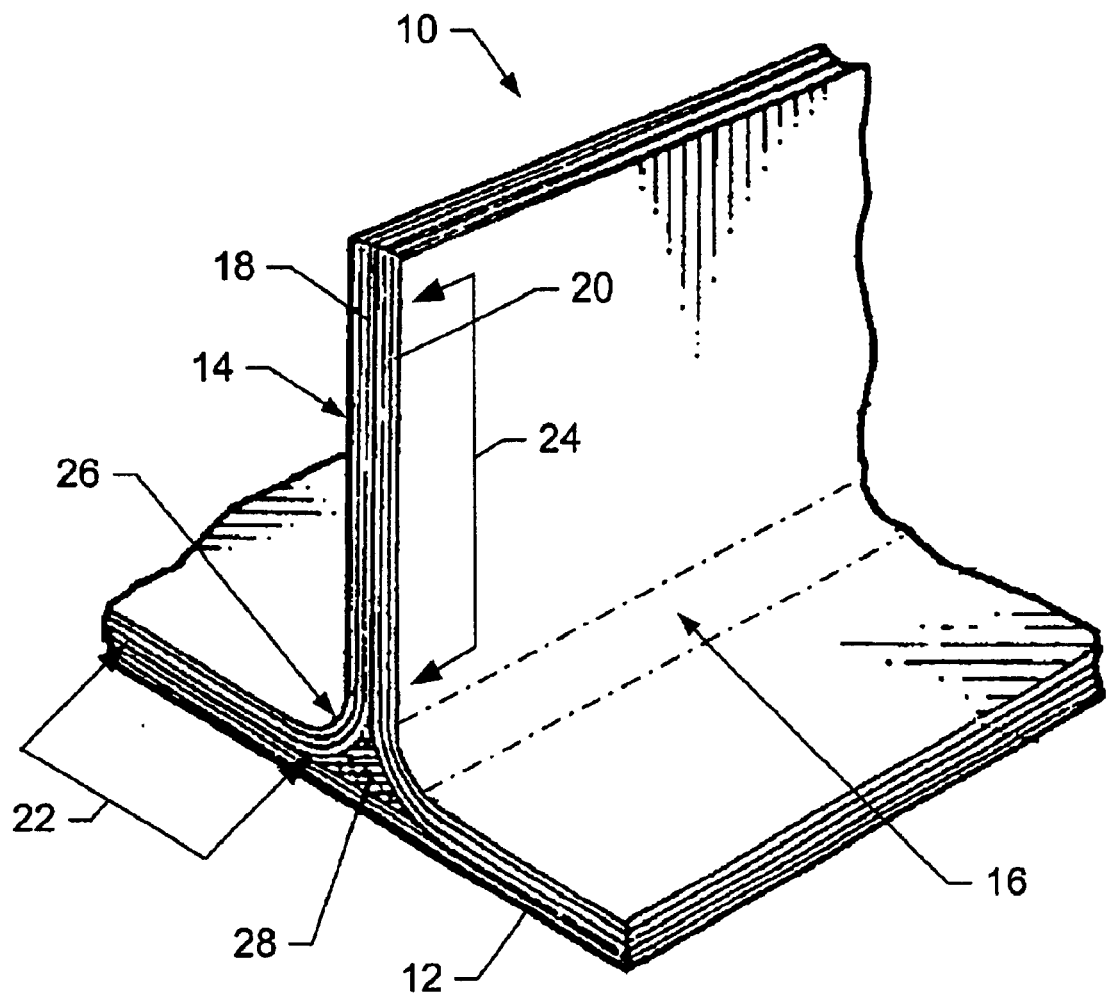
Figure 2:
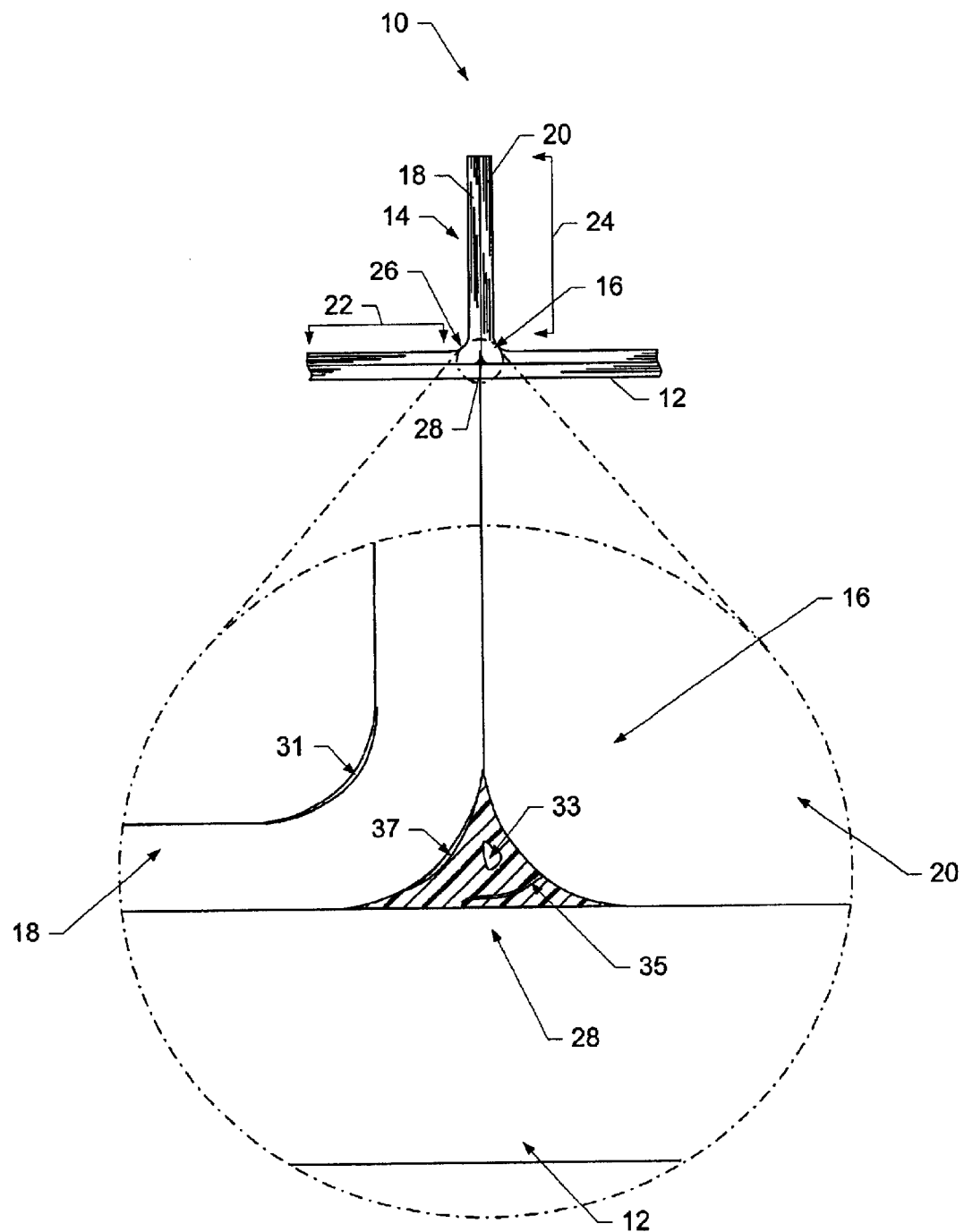
Figure 3:
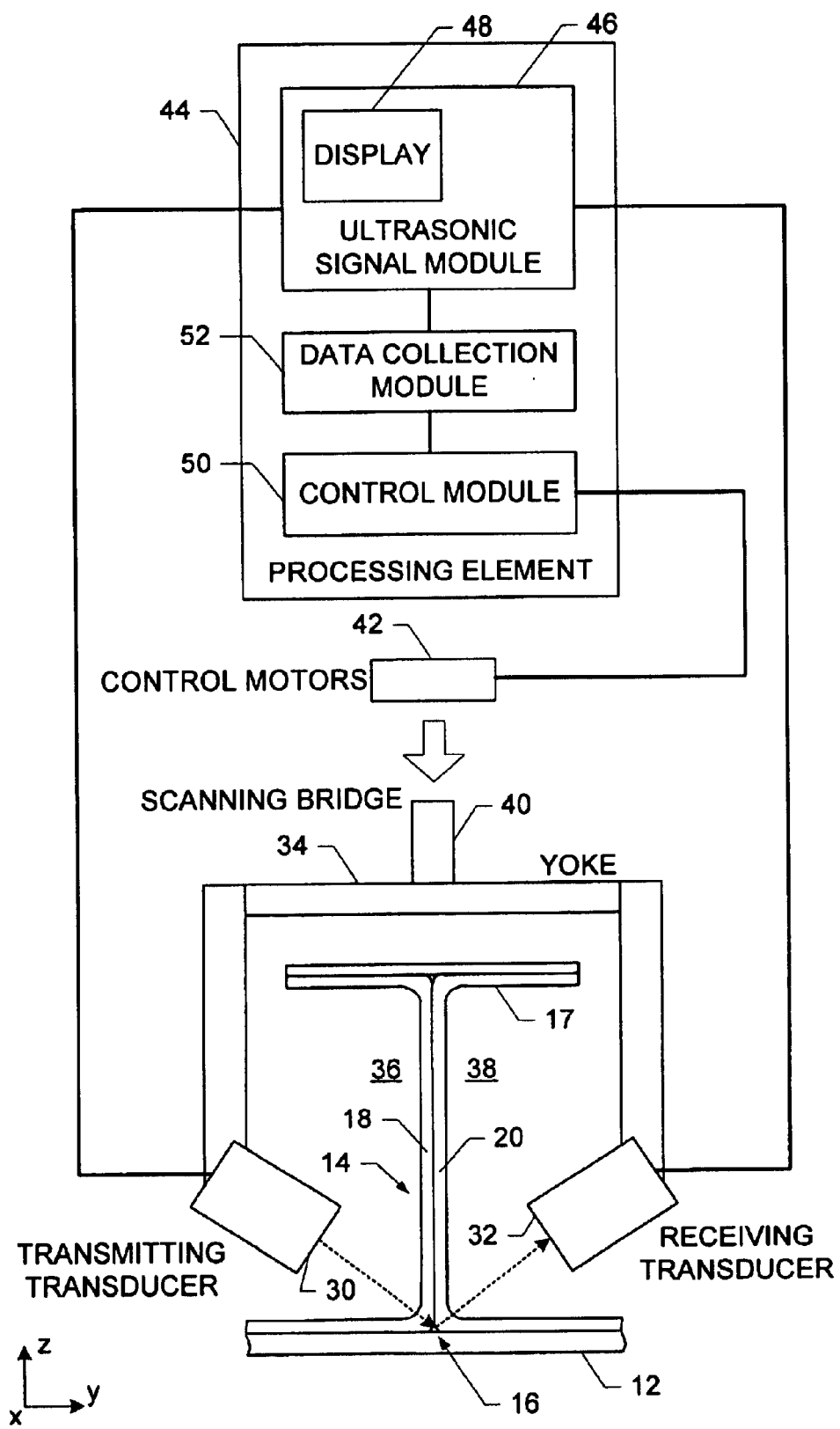
Figure 4:
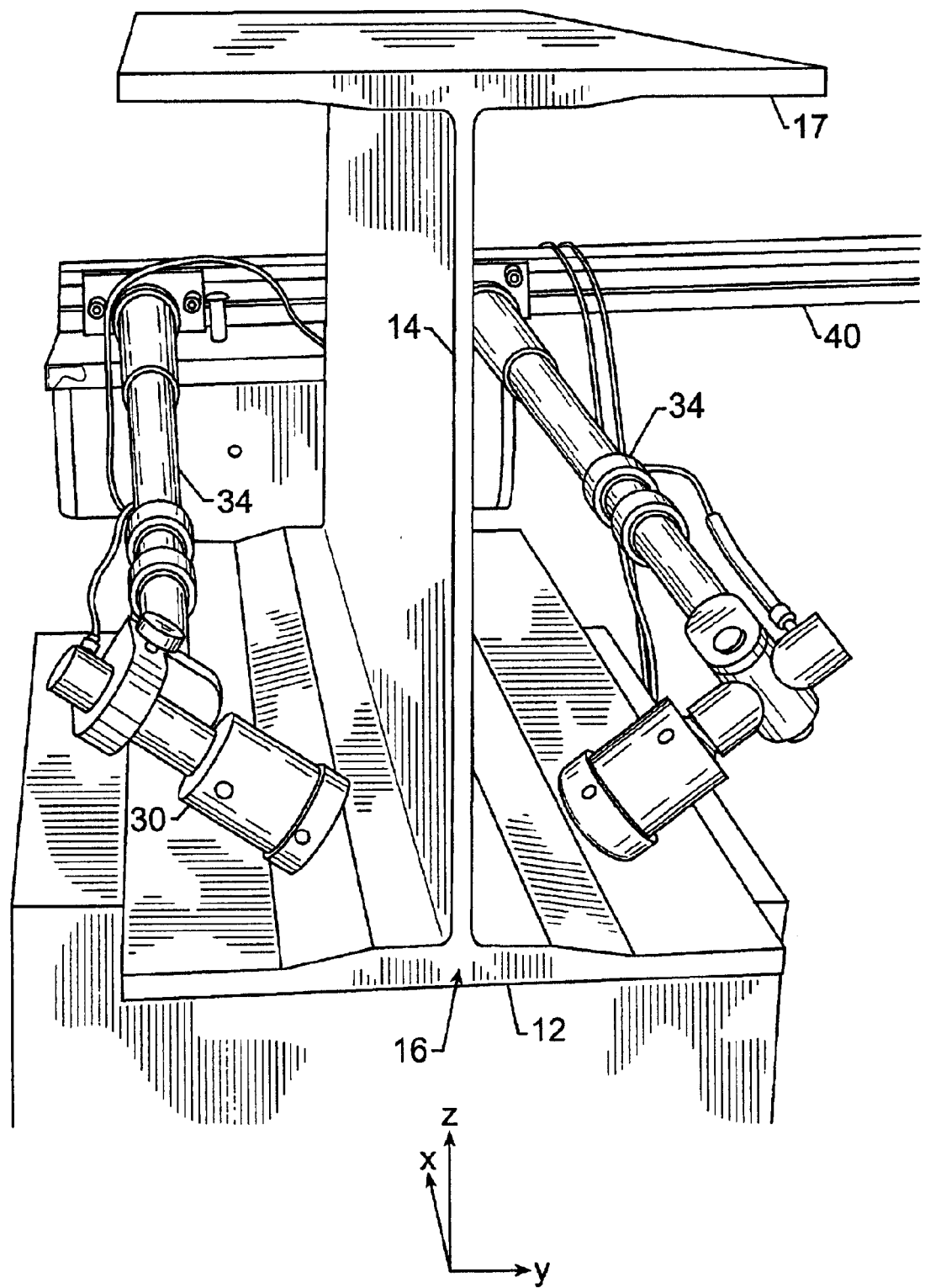
Figure 5:
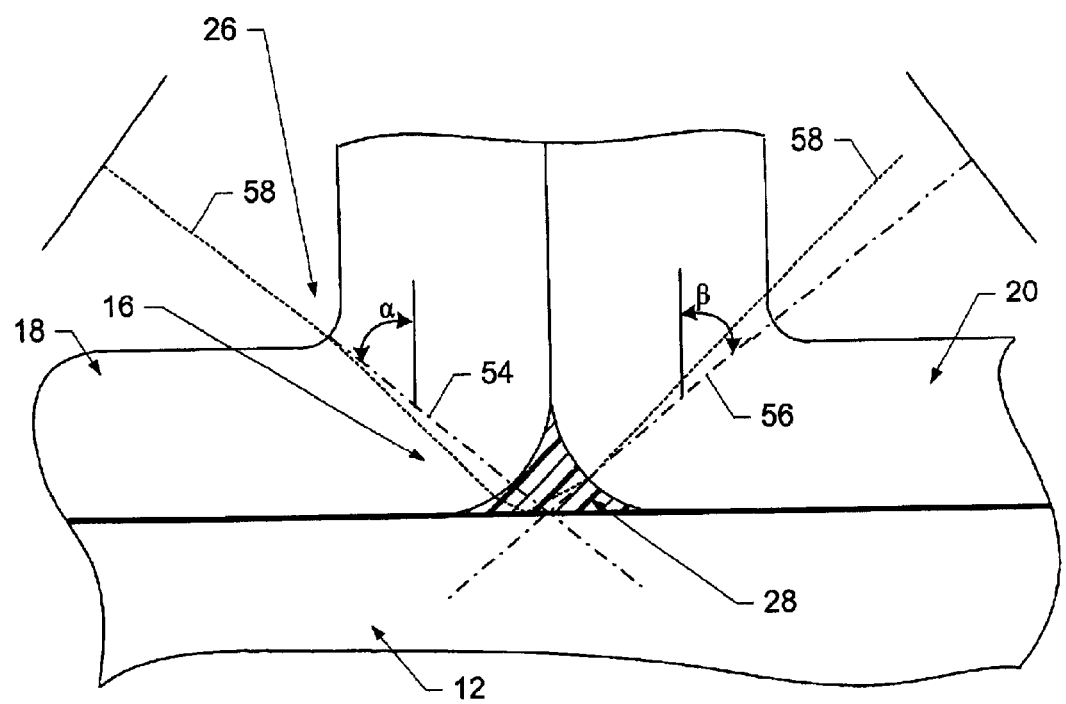
Figure 6:
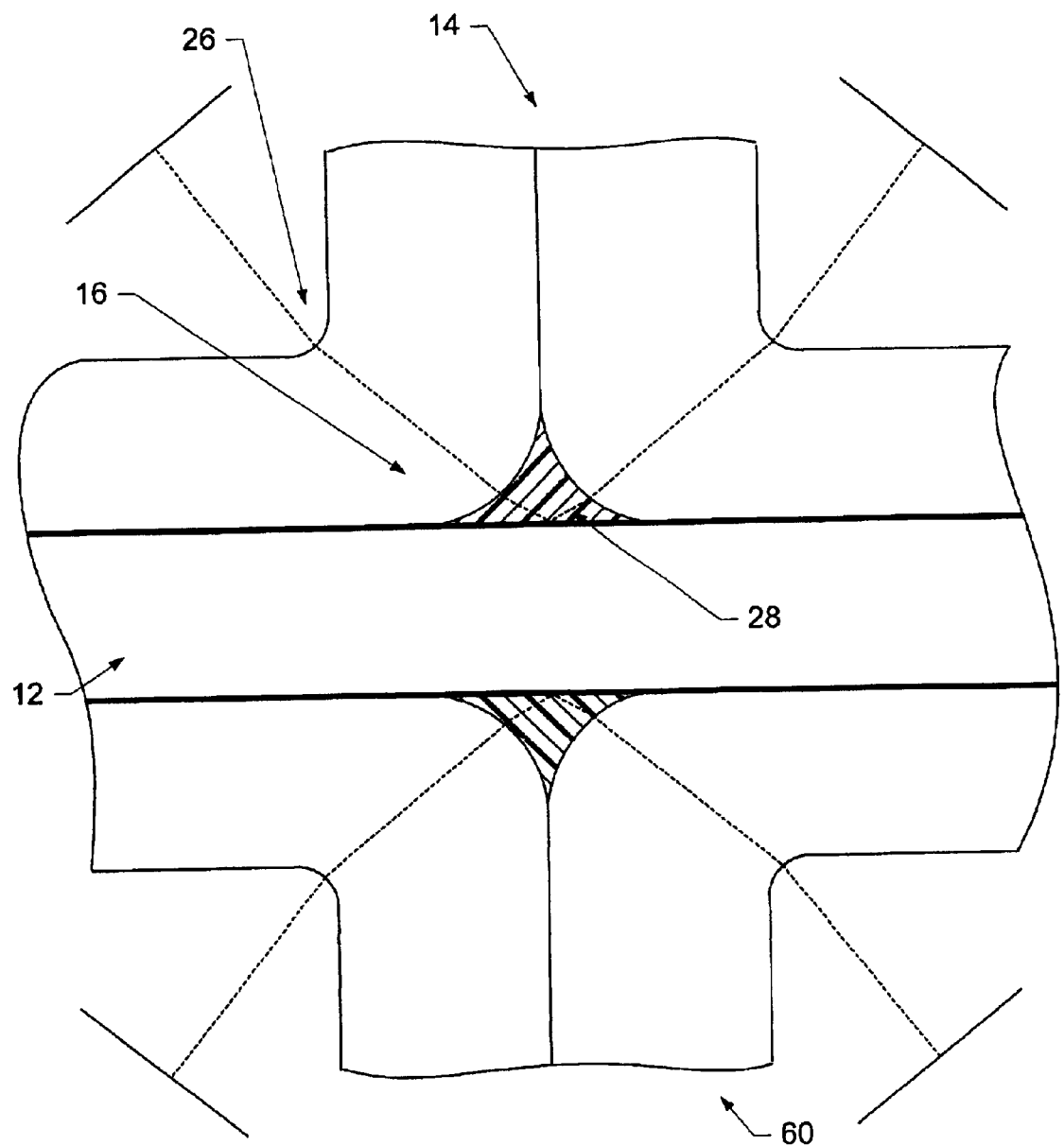

Having thus described the invention in general terms, reference will now be made to the accompanying drawings, which are not necessarily drawn to scale, and wherein:

FIG. 1 is a perspective view of a composite structure including a joint for inspection according to one embodiment of the present invention;

FIG. 2 is a side view with of the composite structure of FIG. 1 with an exploded inset of the joint including various defects that can appear in the joint;

FIG. 3 is a schematic block diagram of a system for inspecting a joint in a composite structure according to one embodiment of the present invention;

FIG. 4 is a perspective schematic illustration of the system including a portion of a scanning bridge according to one embodiment of the present invention;

FIG. 5 is an exploded schematic illustration of the composite structure highlighting the joint according to one embodiment of the present invention; and FIG. 6 is an exploded schematic illustration of another embodiment of the composite structure highlighting the joint.

DETAILED DESCRIPTION OF THE INVENTION

The present invention now will be described more fully hereinafter with reference to the accompanying drawings, in which preferred embodiments of the invention are shown.

This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIGS. 1 and 2, there is shown a reinforced composite structure generally indicated at 10. The composite structure generally comprises a first panel 12, such as skin, and a second panel 14, such as a web, that are connected thereby defining a joint generally indicated at 16. In instances where the first panel comprises a skin and the second panel comprises a web, the web would normally be jointed to an upper panel 17 or spar cap, as shown in FIGS. 3 and 4. The panels can comprise any of a number of elements but, in one embodiment, the panels comprise laminates of a plurality of fiber composite plies. The second panel is made up of opposed composite sheets 18 and 20 (which can each include a number of plies). A base portion 22 of each sheet is positioned parallel and adjacent to the first panel. As can be seen, the base portion 22 of sheet 18 diverges from the corresponding base portion 22 of sheet 20. A upstanding portion 24 of the sheets extends transversely to the first panel. In the embodiment illustrated in FIG. 1, the upstanding portion extends outwardly from the first panel. In this regard, as illustrated, the first and second panels define a T-joint where the upstanding portion of the second panel is disposed approximately orthogonal to the first panel. It should be understood, however, that the upstanding portion can extend from the first panel in any one of a number of different directions without departing from the spirit and scope of the present invention. The sheets of the second panel also have a fillet portion 26 between the base portion and the upstanding portion. The fillet portions of the sheets generally define a gap between the first and second panels at the joint. In this regard, positioned between the sheets of the second panel and the first panel at least partially within the gap is a composite filler material 28, or "noodle," which can be made of resin or adhesive, often reinforced with fabric, chopped composite fiber or the like. To hold the members assembled, a thermosetting adhesive can be placed on the contacting surfaces of the second panel, the first panel and the filler.

As shown in the exploded inset portion of FIG. 2, various defects can appear in the joint defined by the connection of the first and second panels 12 and 14 that affect performance of the composite structure. For example, the joint can include defects such as delaminations 31 in the plies of sheets 18 and 20 of the second panel at the fillet portions 26. Also, for example, the joint can include defects such as voids 33 and/or cracks 35 in the filler, as well as disbonds 37 at the intersections of the filler and the first panel, and/or the filler and the second panel. In this regard, now referring to FIGS. 3 and 4, the present invention provides a system and methods to inspect the joint for such defects. To inspect the joint 16, the system includes a transmitting transducer 30 and a receiving transducer 32 that are capable of transmitting ultrasonic signals into the joint and receiving reflected ultrasonic signals from the joint, respectively. In this regard, defects in the joint can be identified based upon a relationship between the reflected ultrasonic signals and a predetermined threshold, as described below. Advantageously, the transducers are ultrasonic testing (UT) air-coupled transducers and, therefore, do not require a liquid couplant like conventional transducers. In this regard, the system can inspect joints of composite structures that might otherwise be contaminated by a liquid couplant. The transducers can comprise any of a number of known UT air-coupled transducers but, in one embodiment, comprise model AS 400 transducers manufactured by Quality Material Inspection (QMI), Inc. of Costa Mesa, Calif.

To guide the transducers 30 and 32 along the joint so that the entire joint 16 can be inspected, the system includes a scanning assembly. The scanning assembly includes a yoke 34 on which the transmitting and receiving transducers are secured. The yoke has one end disposed proximate composite sheet 18 of the second panel 14, and another end disposed proximate composite sheet 20 of the second panel. In this regard, the transmitting transducer is secured to the end disposed proximate composite sheet 18 thereby defining an input side 36 of the second panel, and the receiving transducer is secured to the end disposed proximate composite sheet 20 thereby defining an output side 38 of the second panel. As shown the input side and output side of the second panel oppose one another and are on a common side of the first panel 12.

The scanning assembly further includes a guide assembly capable of moving the yoke 34 and, thus, the transducers 30 and 32 relative to the joint 16. The guide assembly can comprise any of a number of different elements. For example, the guide assembly can comprise a robotic scanning bridge 40 operated by various control motors 42, such as any of a number of gantry robots controlled by a Cimroc model controller, both manufactured by PaR Systems, Inc. of Shoreview, Minn. In this regard, the scanning bridge can move the yoke/transducers longitudinally along an "x" axis parallel to the length of the joint to inspect along the length of the joint, as well as transversely along a "z" axis parallel to the height of the joint to inspect along the height of the joint. Alternatively, the scanning bridge can move the yoke/transducers laterally along a "y" axis to keep the transducers centered over the joint to thereby inspect the height of the joint. As such, the transducers can transmit and receive the ultrasonic signals and reflected ultrasonic signals for any number of locations on the joint.

While the scanning bridge 40 preferably moves the transducers 30 and 32 along two axes to inspect the joint 16 along the length and height of the joint, the scanning bridge can move the yoke 34 and the transducers along only one of the aforementioned axes to inspect that portion of the joint without departing from the spirit and scope of the present invention. Also, while the scanning bride preferably moves the yoke/transducers along two axes, the scanning bridge can be capable of moving the yoke/transducers along three axes, including the "x", "y", "z" axes. Further, while the yoke and the scanning bridge can comprise separate elements, the yoke and scanning bridge can be embodied in a single device. In this regard, the scanning bridge can comprise a one or two axis robotic scanning bridge, while the yoke comprises an adjustable yoke including two retractable members that are capable of moving the transducers along the "x" axis, as illustrated in FIG. 4.

Again referring to FIG. 3, to identify defects in the joint 16 during inspection, the system includes a processing element 44. Generally the processing element includes an ultrasonic signal module 46 capable of providing electrical pulses to the transmitting transducer, which transmits the ultrasonic signals therefrom. Also, the ultrasonic signal module is capable of receiving electrical pulses from the receiving transmitter, which generates the electrical pulses from the reflected ultrasonic signals received. Further, the signal module can include a display 48, such as a screen, monitor or the like, for displaying the electrical signals provided to and received from the respective transducers.

In addition to the ultrasonic signal module 46, the processing element 44 generally includes a control module 50 for controlling the movement of the scanning bridge 40 and, thus, the yoke 34 and transducers 30 and 32. If so desired, the processing element can also include a data collection module 52 capable of recording and thereafter storing data representative of the amplitudes of the transmitted ultrasonic signals and the received reflected ultrasonic signals. The ultrasonic signal module, control module and data collection module of the processing element can each include separate elements, or one or more of the modules can be embodied in a single device, such as a personal computer, high level processor or the like. For example, in one embodiment, the ultrasonic signal module can comprise an ultrasonic inspection instrument, such as an Airscan Sonda 007CX model air-coupled ultrasonic inspection instrument, manufactured by Quality Material Inspection (QMI), Inc. of Costa Mesa, Calif. Also, for example, the control module and data collection module can collectively be embodied in a personal computer capable of performing the functions of both modules.

In operation, according to one embodiment, the joint 16 of a composite structure 10 is inspected by first calibrating the transducers 30 and 32 relative to one another and the joint. In this regard, reference is now made to FIG. 5. The transmitting transducer is initially set on the input side 36 of the second panel 14 relative to the first panel 12 and the joint. With respect to the first panel, the transmitting transducer is initially such that the axis of transmission 54 of the transmitting transducer is at a predefined angle a with respect to the normal of the first panel, such as forty-five degrees from the normal. And with respect to the joint, the transmitting transducer is initially set at a position such that the axis of transmission 54 of the transmitting transducer intersects a portion of the joint along the length and height of the joint having a high likelihood of not including a defect, such as cracks, voids, delaminations, or porosity in the second panel, filler or first panel at the gap. For example, the transmitting transducer can be initially set such that the axis of transmission intersects a center point along the length and height of the joint or fillet portion of sheet 18 (designated along the "z" axis). Alternatively, a designated "standard" composite structure, which has a similar shape to the one being inspected and a joint with a known non-defective area, can be utilized to calibrate the transducers. In such an instance, the transmitting transducer would then be initially set such that the axis of transmission of the transmitting transducer intersects the known non-defective area of the joint of the standard composite structure.

Once the transmitting transducer 30 is set, the receiving transducer 32 can be oriented on the output side 38 of the second panel 14 with respect to the transmitting transducer and the first panel 14. In this regard, the receiving transducer can be oriented directly opposite the transmitting transducer such that the axis of reception of the receiving transducer 56 has an angle β from the normal of the first panel that equals the same predefined angle α from the normal of the first panel as the transmitting transducer. For example, when the axis of transmission is set at forty-five degrees from the normal of the first panel, the receiving axis of the receiving transducer can likewise be set on the output side of the second panel at forty-five degrees from the normal of the first panel. As such, if both axes of the transducers are set at forty-five degrees from the normal of the first panel, the axis of transmission of the transmitting transducer will orthogonally intersect the axis of reception of the receiving transducer. It should be understood, however, that the predefined angles α and β can be set at any angle relative to the normal of the first panel on the respective side of the second panel, without departing from the spirit and scope of the present invention. In this regard, if the second panel is not perpendicular to the first panel, the predefined angles α and β will necessarily be different for optimum transmission and reception of the ultrasonic signals.

After orienting the receiving transducer 32, the ultrasonic signal module then directs the transmitting transducer to transmit an ultrasonic signal 58 along the axis of transmission 54 of the transmitting transducer into sheet 18 of the second panel 14. Upon entering the second panel, the ultrasonic signal propagates through sheet 18 into the filler 28. Once in the filler, the signal propagates through the filler to an intersection of the filler and the first panel 12 where a significant portion of the ultrasonic signal reflects off of the first panel (with the remaining portion propagating through the first panel). The ultrasonic signal typically transmitted by the transmitting transducer is a longitudinal mode signal, however, at different angles at which the ultrasonic signal propagates through each interface within the composite structure, portions of the ultrasonic signal can undergo a mode conversion into a shear (i.e., transverse) mode signal. In this regard, the ultrasonic signal reflected off the interface of the first panel typically utilized by the system is the reflected longitudinal mode ultrasonic signal.

The reflected ultrasonic signal then proceeds through the filler 28 and sheet 20, exiting at the fillet portion 26 of sheet 20. As shown, however, the reflected portion of the ultrasonic signals may be offline from the axis of reception 56 of the receiving transducer 32 such that the receiving transducer does not receive all of the reflected ultrasonic signal. In embodiments where the ultrasonic signal module 46 includes display 48, such an instance can be seen by a display of the relative amplitudes of the transmitted ultrasonic signal and the reflected ultrasonic signal. If the receiving transducer is offline from the propagation of the reflected ultrasonic signal, the angle of the receiving transducer is adjusted until the receiving transducer can receive most or all of the reflected signals. As described later, an inability to obtain a reflected signal can also signify a defect within the joint 16 (or a point outside the joint). Therefore, if the angle of the receiving transducer is repeatedly adjusted and the receiving transducer still does not receive the reflected signals, the transmitting transducer can be reset such that the axis of transmission intersects another point along the length of the joint or fillet portion 26 of sheet 18.

Once the receiving transducer 32 is aligned with the propagation of the reflected ultrasonic signal, the receiving transducer is secured in place on the yoke 34 in a fixed angular position. After securing the receiving transducer, the yoke, including the transducers, is moved such that the axis of transmission of the transmitting transducer intersects sheet 18 at a first predetermined point at one end of the joint 16 (along the "x" direction). Further, to more completely inspect the height of the joint, the first predetermined point is set a predefined length below the joint such that the axis of transmission of the transmitting transducer intersects the second panel 14 at a point below the joint to thereby define a lower boundary of the inspection envelope. For example, if the joint has a height of 0.50 inches and the transmitting transducer 30 is initially set at a center point along the height of the joint, the yoke can be lowered by 0.25 inches (half the height of the joint) or more (e.g., 0.50 inches), such that the axis of transmission enters the second panel at a point underneath the joint. It should be understood, however, that the first predetermined point need not be set below the joint but, instead, can be set at the lower boundary of the joint.

Once the yoke 34 has positioned the transducers 30 and 32 at one end of the joint 16 below the joint, the ultrasonic signal module 46 directs the transmitting transducer to transmit an ultrasonic signal into the second panel 14 at the point below the joint. The ultrasonic signal will propagate through sheet 18 as before, however, the ultrasonic signal will not intersect the filler 28. And as such, the ultrasonic signal will not propagate to an intersection of the filler and the first panel 12. Therefore, a significant portion of the ultrasonic signal will not reflect off the first panel, but will instead propagate through the first panel exiting the first panel on a side opposite the receiving transducer. As such, the receiving transducer will not receive an appreciable amount of a reflected ultrasonic signal which, as stated before, can be seen by a significant difference in amplitude between the ultrasonic signal transmitted by the transmitting transducer and the reflected ultrasonic signal received by the receiving transducer. In this regard, as the ultrasonic signal is transmitted and the reflected ultrasonic signal is received, the data collection module 52 of the processing element 44 can record and/or save data representative of the transmitted ultrasonic signal and the reflected ultrasonic signal.

After transmitting the ultrasonic signal and receiving any reflected portion of the ultrasonic signal, the control module 50 moves the yoke 34 and, thus, the transducers 30 and 32 longitudinally an incremental amount along the length of the joint 16 (along the "x" axis) such that the axis of transmission of the transmitting transducer intersects the joint at another point. For example, for a joint that has a length of 120 inches, the control module can move the yoke/transducers 0.03 to 0.05 inches along the length. Once the yoke/transducers have been moved, the ultrasonic signal module 46 directs the transmitting transducer to transmit another ultrasonic signal into sheet 18. And as before, because the transmitting transducer is at a height relative to the joint such that the axis of transmission intersects sheet 18 at a point below the joint, the receiving transducer will not receive an appreciable portion of the reflected ultrasonic signal. As before, the data collection module 52 again records and/or saves data representative of the transmitted ultrasonic signals and the reflected ultrasonic signals. The control module then repeatedly moves the yoke/transducers along the length, with the transducers transmitting and receiving ultrasonic signals and reflected portions of the ultrasonic signals, respectively. And the data collection module records and/or saves respective data at each point. By transmitting/receiving the ultrasonic signals, recording the data and moving the yoke/transducers, the system can scan the length of the joint at the set position below the joint.

After scanning the length of the joint 16, the control module 50 can move the yoke/transducers such that the axis of transmission of the transmitting transducer 32 intersects sheet 18 at a point a predefined height above the previously set position below the joint. For example, with a joint having a height of 0.50 inches, the control module can move the yoke/transducers such that the axis of transmission intersects sheet 18 at a point 0.03 to 0.05 inches above the previously set position. The system again scans the length of the joint with each point in which an ultrasonic signal is transmitted being the predefined height above respective points in the previously scanned length.

The control module 50 again moves the yoke/transducers the predefined height such that the system can scans the length again, with the control module continuously scanning the length of the joint at points along the height of the joint. As the control module moves the yoke/transducers such that the axis of transmission of the transmitting transducer begins to intersect the joint, a significant portion of the ultrasonic signals transmitted into sheet 18 will reflect off of the first panel 12 at the intersection of the first panel and the filler 28 as before with respect to calibrating the transducers 30 and 32. As such, in a non-defective portion of the joint, the receiving transducer will receive a reflected ultrasonic signal having an amplitude above a predefined threshold. If the transmitting transducer transmits an ultrasonic signal into a defective portion of the joint, however, a significant portion of the ultrasonic signal will propagate through the first panel with the receiving transducer receiving a reflected ultrasonic signal below the threshold. Additionally, or alternatively, the data collected by the data collection module 52 representative of the reflected ultrasonic signals received by the receiving transducer can be used to produce an image of the joint that can be examined, such as by an operator, for defects. Although an image of the joint is not necessary for flaw detection, such an image can be used to determine the size and/or shape of the defect, which can then be analyzed and reproduced from the respective data at the end of the inspection.

The threshold can be defined in any one of a number of different manners but, in one embodiment, the threshold is defined based upon the amplitude of the ultrasonic signal transmitted by the transmitting transducer 30. For example, the threshold can be defined to equal half of the amplitude of the ultrasonic signal transmitted. Thus, if the receiving transducer 32 receives a reflected ultrasonic signal more than half the transmitted signal, the respective portion of the joint is deemed not defective. But if the receiving transducer receives a reflected ultrasonic signal less than half the transmitted signal, the respective portion is identified as defective.

The control module 50 continues to move the yoke/transducers, while the system repeatedly scans the length of the joint 16 at different heights, preferably until the system has scanned the length of the joint a predetermined distance above the joint. In this regard, the predetermined distance above the joint can define the upper boundary of the inspection envelope. The predetermined distance can be set at any distance above the joint but, in one embodiment, the predetermined distance is set such that the upper boundary and the lower boundary are equidistant from the center of the joint. Similar to the lower boundary, however, the upper boundary need not be set above the joint but, instead, can be set at the upper boundary of the joint.

At this point it should be understood that while the system scans the length of the joint 16, transmitting and receiving ultrasonic signals along the length of the joint for points below the joint up through the height of the joint to points above the joint, such is only one method by which the system can inspect the joint. In this regard, the system can scan the height of the joint between the upper and lower boundaries of the inspection envelope and move along the length a predetermined length thereafter to scan the joint. Alternatively, the system can scan the joint and the points within the inspection envelope in any other systematic or nonsystematic manner, so long as the ultrasonic signals are transmitted into sheet 18 and thereafter received for points along the length of the joint.

Further, while the embodiment of the composite structure illustrated in FIGS. 1–5 generally includes what is known as a T-joint, it should be understood that the composite structure can comprise any of a number of different composite structures including a joint in which a filler is disposed. For example, referring now to FIG. 6, in another embodiment, the composite structure comprises an X-joint. The X-joint generally includes the first and second panels, as well as the filler. But in contrast to the T-joint, the X-joint further includes a third panel 60. Generally, the third panel has a configuration similar to the second panel, and is disposed proximate a side of the first panel opposite the second panel. As such, the joint between the first and second panels can be inspected as provided above. In addition, the joint between the first and third panels can be inspected in a similar manner, either with the composite structure turned upside down or with the transducers repositioned with respect to the joint between the first and third panels. As such, the system and methods of the present invention may advantageously inspect joints in composite structures having various configurations, including composite structures having T and X-shapes so long as the composite structure includes a pair of panels connected in a manner to define a joint in which a filler is disposed.

The system and methods of the present invention therefore reliably detect defects within the joint, while overcoming the drawbacks of other automated inspection systems. In this regard, the system and methods can inspect the joint without the use of couplants that could contaminate the composite structure. Further, the system of the present invention is inexpensive to manufacture, when compared to conventional automated systems. And the system and methods of the present invention are inexpensive to implement, as compared to conventional automated inspection systems and methods.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for inspecting a joint in a composite structure that includes first and second panels that are connected thereby defining the joint, wherein the second panel at least partially extend outwardly from the first panel at the joint, and wherein the composite structure further includes filler disposed at the joint, said system comprising:

a transmitting transducer disposed proximate an input side of the second panel, said transmitting transducer being capable of transmitting an ultrasonic signal into the second panel such that at least a portion of the ultrasonic signal reflects off of the first panel at the joint and exits an output side of the second panel, wherein the input and output sides are on opposite sides of the second panel and are located on a common side of the first panel;

a receiving transducer disposed proximate the output side of the second panel, said receiving transducer being capable of receiving the reflected portion of the ultrasonic signal; and a processing element in electrical communication with the transmitting and receiving transducers, wherein the transmitting and receiving transducers are capable of being guided along a length and a height of the joint such that the processing element is capable of identifying a defect in the composite structure based upon a relationship of the reflected portion of the ultrasonic signal received by said receiving transducer to a predetermined threshold.

2. A system according to claim 1, wherein the filler is disposed between and at least partially contacts both the first and second panels, wherein said transmitting transducer is capable of transmitting an ultrasonic signal into the filler at an interface of the filler and the second panel such that at least a portion of the ultrasonic signal reflects off of the first panel at an interface of the first panel and the filler.

3. A system according to claim 1, wherein said processing element is capable of identifying a defect based upon a comparison of the reflected portion of the ultrasonic signal and the predetermined threshold, and wherein the predetermined threshold is based upon the ultrasonic signal transmitted by said transmitting transducer.

4. A system according to claim 3, wherein said processing element is capable of identifying a defect when the reflected portion of the ultrasonic signal is less than a predetermined percentage of the ultrasonic signal transmitted by said transmitting transducer.

5. A system according to claim 1, wherein the second panel defines a gap at the joint, wherein the filler is disposed within the gap, and wherein said transmitting transducer is capable of transmitting the ultrasonic signal into the filler within the gap such that at least a portion of the ultrasonic signal reflects off the first panel at an interface of the filler and the first panel.

6. A system according to claim 5, wherein the second panel includes a base portion, an upstanding portion and a fillet portion joining the base and upstanding portions, wherein the base portion is disposed parallel to the first panel and the upstanding portion extends outwardly from the first panel, and herein said transmitting transducer is capable of transmitting the ultrasonic signal into the filler at the fillet portion of the second panel.

7. A system according to claim 1, wherein the first and second panels each comprise a plurality of plies that are adhesively bonded together, wherein the second panel includes two opposed sheets, wherein each sheet comprises a plurality of plies and has a base portion, an upstanding portion and a fillet portion joining the base and upstanding portions, wherein the base portions of the sheets are disposed parallel to the first panel and diverge from one another, and the upstanding portions extend outwardly from the first panel, and wherein said transmitting transducer is capable of transmitting the ultrasonic signal into the fillet portion of one of the sheets such that at least a portion of the ultrasonic signal reflects off of the first panel at the joint and exits the fillet portion of the other sheet.

8. A system according to claim 7, wherein the fillet portions of the sheets of the second panel define a gap at the joint, wherein the filler is disposed within the gap, and wherein said transmitting transducer is capable of transmitting the ultrasonic signal into the filler within the gap such that at least portion of the ultrasonic signal reflects off the first panel at an interface of the filler and the first panel.

9. A system according to claim 1 further comprising a scanning assembly electrically connected to said processing element, wherein said transmitting and receiving transducers are secured to said scanning assembly such that said scanning assembly guides said transmitting and receiving transducers along the joint.

10. A system according to claim 9, wherein said scanning assembly comprises:

a yoke having one end disposed proximate the input side of the second panel and another end disposed proximate the output side of the second panel, wherein said transmitting transducer is secured to the end of the yoke proximate the input side, and wherein said receiving transducer is secured to the end of the yoke proximate the output side; and a guide assembly capable of moving said yoke relative to the composite structure.

11. A method for inspecting a joint in a composite structure comprising:

providing a composite structure that includes first and second panels that are connected thereby defining a joint, wherein the second panel extends outwardly from the first panel at the joint, and wherein the composite structure further includes a filler disposed at the joint;

guiding a transmitting transducer and a receiving transducer along a length and a height of the joint, and while guiding the transmitting and receiving transducers, transmitting an ultrasonic signal from the transmitting transducer into an input side of the second panel such that at least a portion of the ultrasonic signal reflects off of the first panel at the joint and exits an output side of the second panel, wherein the input and output sides are on opposite sides of the second panel and are located on a common side of the first panel;

receiving the reflected portion of the ultrasonic signal at the receiving transducer on the output side of the second panel; and identifying a defect in the composite structure based upon a relationship between the reflected portion of the ultrasonic signal received and a predetermined threshold.

12. A method according to claim 11, wherein the filler is disposed between and at least partially contact both the first and second panels, wherein transmitting an ultrasonic signal comprises transmitting an ultrasonic signal into the filler at an interface of the filler and the second panel such that at least a portion of the ultrasonic signal reflects off of the first panel at an interface of the second panel and the filler.

13. A method according to claim 11, wherein identifying a defect comprises identifying the defect based upon a comparison of the reflected portion of the ultrasonic signal and the predetermined threshold, and wherein the predetermined threshold is based upon the ultrasonic signal transmitted.

14. A method according to claim 13, wherein identifying a defect comprises identifying the defect when the reflected portion of the ultrasonic signal is less than a predetermined percentage of the ultrasonic signal transmitted.

15. A method according to claim 11, wherein providing the composite structure comprises providing a composite structure including a second panel that defines a gap at the joint, wherein the filler is disposed within the gap, and transmitting an ultrasonic signal comprises transmitting the ultrasonic signal into the filler within the gap such that at least a portion of the ultrasonic signal reflects off the first panel at an interface of the filler and the first panel.

16. A method according to claim 15, wherein providing the composite structure comprises providing a composite structure including a second panel that includes a base portion, an upstanding portion and fillet portion joining the base and upstanding portions, wherein the base portion is disposed parallel to the first panel and the upstanding portion extends outwardly from the first panel, and wherein transmitting an ultrasonic signal comprises transmitting the ultrasonic signal into the filler at the fillet portion of the second panel.

17. A method according to claim 11, wherein transmitting an ultrasonic signal comprises selecting a first predetermined point on the input side of the second panel and thereafter transmitting the ultrasonic signal into the predetermined point such that at least a portion of the ultrasonic signal reflects off of the first panel at the joint, and wherein receiving the reflected portion comprises receiving the reflected portion of the ultrasonic signal at an associated point on the output side o the second panel, said method further comprising:

repeatedly selecting different points on the input side of the second panel, wherein transmitting the ultrasonic signal an receiving the reflected portion occur for each point selected, wherein identifying a defect comprises identifying a defect at each point based upon a relationship between the reflected portion of the ultrasonic signal received at the respective associated point and a predetermine threshold.

18. A method for inspecting a joint in a composite structure comprising:

providing a composite structure that includes first and second panels that are connected thereby defining a joint, wherein the second panel includes two opposing sheets, wherein each sheet has a base portion, an upstanding portion and a fillet portion joining the base and upstanding portions, wherein the base portions of the sheets are disposed parallel to the first panel on a common side of the first panel and diverge from one another, and the upstanding portions extend outwardly from the first panel, wherein the fillet portions define a gap between the second panel and the first panel at the joint, and wherein the composite structure further includes a filler disposed in the gap;

guiding a transmitting transducer and a receiving transducer along a length and a height of the joint, and while guiding the transmitting and receiving transducers, transmitting an ultrasonic signal from the transmitting transducer into the filler at the fillet portion of one of the sheets of the second panel such that at least a portion of the ultrasonic signal reflects off of the first panel at the joint and exits the second panel at the fillet portion of the other sheet;

receiving the reflected portion of the ultrasonic signal at the receiving transducer; and identifying a defect in the composite structure based upon a relationship of the reflected portion of the ultrasonic signal received to a predetermined threshold.

19. A method according to claim 18, wherein the filler is disposed between and at least partially contact both the first and second panels, wherein transmitting an ultrasonic signal comprises transmitting an ultrasonic signal into the filler at an interface of the filler and the second panel such that at least a portion of the ultrasonic signal reflects off of the first panel at an interface of the first panel and the filler.

20. A method according to claim 18, wherein identifying a defect comprises identifying the defect based upon a comparison of the reflected portion of the ultrasonic signal and the predetermined threshold, and wherein the predetermined threshold is based upon the ultrasonic signal transmitted.

21. A method according to claim 20, wherein identifying a defect comprises identifying the defect when the reflected portion of the ultrasonic signal is less than a predetermined percentage of the ultrasonic signal transmitted.

22. A method according to claim 18, wherein the fillet portions of the sheets of the second panel define a longitudinally extending gap, wherein transmitting an ultrasonic signal comprises selecting a first predetermined point on the fillet portion of an input sheet of the second panel and thereafter transmitting the ultrasonic signal into the first predetermined point, said method further comprising:

repeatedly selecting points longitudinally spaced from the first predetermined point on the fillet portion of the input sheet of the second panel along the length of the gap, wherein transmitting the ultrasonic signal and receiving the reflected portion occur for each point selected, wherein identifying a defect comprises identifying a defect at each point based upon a relationship between each reflected portion of the ultrasonic signal received and a predetermined threshold.

23. A method according to claim 22 further comprising selecting, for each longitudinally spaced point, a plurality of points spaced apart in a transverse direction, wherein transmitting the ultrasonic signal and receiving the reflected portion occur for each point selected.

\* \* \* \* \*